United States Patent [19]

Brandman et al.

[11] 4,170,704

[45] Oct. 9, 1979

[54] IODOPROPARGYL PYRIDYL AND PICOLINYL ETHERS AND THIOETHERS AS PAINT FUNGICIDES

[75] Inventors: Harold A. Brandman, Glen Ridge; Joachim E. Freudewald, Morristown; Milton Manowitz, Fair Lawn; Edward J. Nikawitz, Glen Rock; Frederick H. Sharpell, Jr., Pequannock, all of N.J.

[73] Assignee: Givaudan Corporation, Clifton, N.J.

[21] Appl. No.: 898,759

[22] Filed: Apr. 20, 1978

[51] Int. Cl.$^2$ .................. C07D 213/02; C07D 213/30; C07D 213/32

[52] U.S. Cl. .................................... 546/290; 546/297; 546/303; 546/339; 106/15.05

[58] Field of Search .......... 260/294.86, 297 R, 296 R, 260/29.6 MN, 290 HL; 546/290, 297, 303, 339

[56] References Cited

U.S. PATENT DOCUMENTS

| | | | |
|---|---|---|---|
| 3,535,328 | 10/1970 | Zielinski | 260/295 AM |
| 3,892,699 | 7/1975 | Weisse | 260/29.6 MN |
| 3,907,797 | 9/1975 | Budesinky et al. | 260/251 R |

*Primary Examiner*—Alan L. Rotman
*Attorney, Agent, or Firm*—Robert F. Tavares; Thomas Cifelli, Jr.

[57] ABSTRACT

Novel iodopropargyl pyridyl and picolinyl ethers and thioethers are effective antifungal agents. They find special utility in paint for protecting finished paint films from fungal attack.

26 Claims, No Drawings

IODOPROPARGYL PYRIDYL AND PICOLINYL ETHERS AND THIOETHERS AS PAINT FUNGICIDES

BACKGROUND OF THE INVENTION

1. Field of the Invention

Pyridyl and picolinyl iodopropargyl ethers as paint fungicides.

2. Prior Art

U.S. Pat. No. 3,907,797 discloses the present state of the art concerning 3-iodinepropargylaryl, 3-iodinepropargylbenzyl and 5-(3-iodinepropargyloxy)pyrimidines and their antibiotic and antimycotic properties.

SUMMARY OF THE INVENTION

The novel iodopropargyl pyridyl and picolinyl ethers and thioethers of this invention can be represented by the general formula:

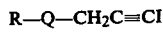

wherein Q is oxygen or sulfur and R is a pyridyl or picolinyl radical which may or may not be substituted.

The novel compounds are effective angtifungal agents and have been found to be surprisingly effective in protecting finished paint films from mildew attack for extended periods.

The novel compounds are normally prepared by alkylating a suitable pyridyl or picolinyl alcohol or thiol with a propargyl halide to form an ether which is subsequently iodinated. The synthesis is illustrated below.

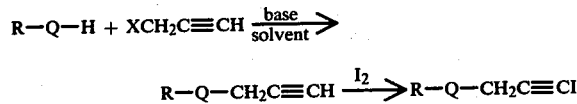

DESCRIPTION OF THE PREFERRED EMBODIMENTS

The data indicate that compounds having the general formula,

(Q being oxygen or sulfur, and R being a pyridyl or picolinyl radical) have general antifungal activity. The data also indicate that substituents on the aromatic ring such as hydrogen, halogen, lower alkyl or amino do not materially affect the level of antifungal activity.

Certain compounds are presently preferred for economic reasons. For example, those compounds wherein Q is oxygen and wherein R is a 3-pyridyl or 3-picolinyl group are prepared from more readily available starting materials and therefore appear more attractive commercially.

The data also indicate that those compounds wherein Q is oxygen are more resistant to decomposition or general inactivation by heat and light then those wherein Q is sulfur. Since exterior latex paint would be exposed to both heat and light, the oxygen ethers would be preferred to the sulfur ethers as agents to prevent the attack of mildew on exterior painted surfaces.

It is a most surprising and unexpected finding of this invention that actual field testing over a six month period indicates that a number of iodopropargyl 3-pyridyl ethers are significantly superior to known commercial paint fungicides; these novel compounds keeping the painted surfaces mildew free for longer periods of time.

The compounds of this invention can be prepared by first reacting a pyridyl or picolinyl alcohol with a propargyl halide by methods similar to those illustrated in the examples. There are also a number of methods known in the art for preparing propargyl ethers from alcohols and phenols which could be adapted to the present invention.

The propargyl ethers can then be converted to iodopropargyl ethers by methods similar to those known in the art and as illustrated in the examples provided herein.

The novel mildewcides of this invention may be incorporated into the paint in a variety of ways. It is expected that those skilled in the art would determine the preferred method of introducing it in the paint. Among the methods available are introducing the fungicide as the paint is blended, mulling the fungicide into the paint, introducing a solution of the fungicide into the paint, etc.

Normally the concentration of the novel mildewcide in the paint will be less than 1.0%. Higher amounts, though operable, would not be economical.

An amount of the novel mildewcide at a concentration level of 0.1% to 1.0% in the liquid paint would suffice for most purposes. A concentration of about 0.2% to 0.7% is preferred for most applications, with about 0.5% being especially preferred.

ILLUSTRATION OF PREFERRED EMBODIMENTS

The following examples are included to illustrate the preferred embodiments of this invention and should not be construed as limiting. They are intended to embrace any equivalents or obvious extensions which are known or should be known to persons skilled in the art.

A. The first set of examples illustrates the preparation of the novel compounds of this invention.

EXAMPLE I

Preparation of 3-(2-propynyloxy)pyridine—Method A

The potassium salt of 3-hydroxypyridine (108 g, 0.81 mol) was dissolved in dry N,N-dimethylformamide (800 ml). (The salt was prepared by refluxing equimolar amounts of 3-hydroxypyridine and potassium hydroxide in toluene with separation of water). The solution was cooled to 10° C. and propargyl chloride (70 g, 0.92 mol) added at that temperature. The reaction mixture was stirred an additional 90 min., poured into 800 ml. water, and then extracted three times with 800 ml ether. The combined ether extract was washed three times with water, dried over anhydrous magnesium sulfate, filtered and concentrated to give 47.0 g of an oil. Analysis by vpc showed this material to be 94.5% pure (3-(2-propynyloxy) pyridine yield 41.7% of theory; b.p. 70°-75° C. (1.2 mm); nmr and ir compatible with structure.

EXAMPLE II

Preparation of 2-chloro-3-(propynyloxy)pyridine

To a solution of 15.6 g (0.12 mole) 2-chloro-3-pyridinol in 200 ml DMF were added 6.7 g (0.12 mole) powdered potassium hydroxide. After cooling to 15° C., 9.0 g (0.12 mole) propargyl chloride was added dropwise. This mixture was stirred at room temperature for 2 hrs., then 200 ml water and 400 ml ether were added. After agitating, the organic layer was separated, dried over anhydrous magnesium sulfate, filtered and concentrated to leave 16.0 g crude product. Recrystallization from hexane gave 10.5 g pure 2-chloro-3-(2-propynyloxy)pyridine, mp 78°–79°.

Analysis calculated for: $C_8H_6ClNO$: C, 56.40; H, 3.60; N, 8.36. Found: C, 56.67; H, 3.55; N, 8.51.

EXAMPLE III

Preparation of 2-chloro-6-methyl-3-(2-propynyloxy)pyridine

In a manner similar to Example I, 2-chloro-6-methyl-3-hydroxypyridine was converted to 2-chloro-6-methyl-3-(2-propynyloxy)pyridine, b.p. 95° C. (0.7 mm).

Analysis calculated for: $C_9H_8ClNO$: C, 59.51; H, 4.44; N, 7.71. Found: C, 59.32; H, 4.23; N, 7.58.

The 2-chloro-6-methyl-3-hydroxypyridine was prepared from 6-methyl-3-hydroxypyridine according to the following procedure:

In 500 ml conc. hydrochloric acid was dissolved 50.0 g (0.46 mole) 6-methyl-3-hydroxypyridine. After heating to 80° C., 150 ml 15% hydrogen peroxide was slowly added over several hours while maintaining the reaction temperature at 80°–85°. The reaction mixture was cooled to 50° C. and concentrated under reduced pressure. The residue was brought to pH 8 by careful addition of 25% sodium hydroxide solution. This mixture was extracted with ether. The solvent was removed and the residue recrystallized one time from water and one time from benzene to provide pure 2-chloro-6-methyl-3-hydroxypyridine, mp 190°–191° C.
CL EXAMPLE IV

Preparation of 2-amino-3(2-propynyloxy)pyridine

In a manner similar to Example I, 2-amino-3-hydroxypyridine was converted to 2-amino-3(2-propynyloxy)pyridine, b.p. 150° C. (0.4 mm). Nmr and ir were compatible with the structure.

EXAMPLE V

Preparation of 3-(2-propynyloxy)pyridine—Method B

To a mixture of 9.5 g (0.1 mole) 3-hydroxypyridine, 5.2 g (0.1 mole) sodium methylate and 150 ml N,N-dimethylformamide, there was added 12.0 g (0.1 mole) propargyl bromide at room temperature over a two hour period. Most of the solvent was removed under reduced pressure. The residue was taken up with 200 ml methylene chloride and 100 ml water, the layers were separated and the methylene chloride evaporated to give 4.5 g 3-(2-propynyloxy)pyridine, yield 34%.

EXAMPLE VI

Preparation of 6-methyl-3-(2-propynyloxy)pyridine

To a solution of 25.0 g (0.229 mole) 3-hydroxy-6-methylpyridine in 200 ml DMSO there was added 12.8 g (0.22 mole) powdered potassium hydroxide and 20.0 g (0.266 mole) propargyl chloride. The mixture was stirred at room temperature for 6 hrs. and then poured into an equal volume of water. This mixture was extracted with ether. The ether extract was dried, filtered and concentrated to have 20.5 g crude product. Distillation gave 16.2 g 6-methyl-3-(2-propynyloxy)-pyridine. Yield 48% theory; b.p. 75° C. (1.0 mm); mp 32°–34° C.

Analysis calculated for: $C_9H_9NO$: C, 73.45; H, 6.16; N, 10.87. Found: C, 73.56, H, 5.98; N, 10.79.

EXAMPLE VII

Preparation of 3-(2-propynyloxymethyl)pyridine

While maintaining the reaction mixture at 5°–10° C., 3-pyridylcarbinol (50.0 g, 0.45 mol) was slowly added to a mixture of sodium hydride (24.0 g of a 50% suspension in mineral oil, 0.5 mol) in 250 ml dry N,N-dimethylformamide. Propargyl chloride (37.0 g, 0.5 mole) was then slowly added to this mixture at 15° C. Following the addition, the reaction mixture was warmed to 35° and maintained for 15 mins at this temperature. The reaction was then cooled to 15°–20°, carefully quenched by dropwise addition of water and extracted with ether. The combined ether extracts were dried over anhydrous magnesium sulfate, filtered and concentrated under reduced pressure to give 45 g crude product. Distillation gave 30.0 g of 3-(2-propynyloxymethyl) pyridine. Yield 44% theory; b.p. 95° C. (0.9 mm).

Analysis calculated for: $C_9H_9NO$: C, 73.45; H, 6.16; N, 9.52 Found: C, 73.41; H, 6.26; N, 9.52.

EXAMPLE VIII

Preparation of 4-(2-propynyloxy)pyridine

To a solution of 20.0 g (0.21 mole) 4-hydroxypyridine and 200 ml dimethyl sulfoxide was added 102 g (0.1 mole) silver carbonate. Propargyl chloride (22.5 g, 0.3 mole) was added to this suspension and the mixture heated at 50° for 6 hrs. After cooling to room temperature, the reaction mixture was diluted with water and extracted two times with ether. The combined ether extract was dried, filtered and concentrated as before to give 1.0 g of 4-(propynyloxy)pyridine. The product was 95% pure by vpc. The nmr and ir were compatible with the structure.

EXAMPLE IX

Preparation of 4-(2-propynylthio)pyridine

In 200 ml dimethyl sulfoxide (DMSO) was dissolved 25.0 g (0.225 mole) 4-mercaptopyridine. To this solution were added 15.5 g (0.112 mole) anhydrous potassium carbonate and 16.5 g (0.25 mole) propargyl chloride. This mixture was heated at 60° C. for 3 hours. The reaction mixture was then cooled to room temperature and filtered. The filtrate was added to an equal volume of water. This mixture was extracted with ether. After removal of the ether under reduced pressure, there remained 20.0 g crude product. Distillation gave 13.5 g 4-(2-propynylthio)pyridine. Yield 39% theory; b.p. 79°–81° C. (1.0 mm); mp 55°–56° C.

Analysis calculated for: $C_8H_7NS$: C, 64.30; H, 4.73; N, 9.36 S, 21.43. Found: C, 63.76; H, 4.60; N, 9.36; S, 21.04.

EXAMPLE X

Preparation of 3-(2-propynylthio)pyridine

In a manner similar to Example IX, 3-mercaptopyridine was converted to 3-(2-propynylthio)pyridine, b.p. 80°–90° C. (1.0 mm).

Analysis calculated for: $C_8H_7NS$: C, 64.38; H, 4.37; N, 9.36; S, 21.43. Found: C, 64.18; H, 4.66; N, 9.60; S, 21.85.

EXAMPLE XI

Preparation of 3-(3-iodo-2-propynyloxy)pyridine

In 300 ml methanol was dissolved 39.0 g (0.27 mole) 3-(2-propynyloxy)pyridine. This solution was cooled to 0° C. and 54.0 g (1.35 moles) sodium hydroxide was added slowly while maintaining the temperature at 0°-5° C. Iodine (82.0 g, 0.32 mole) was added portionwise followed by the addition of 400 ml methanol. After stirring for 2 hours at room temperature, the reaction mixture was poured into cold water. The resulting precipitate was filtered and dried. This crude product was recrystallized from 350 ml methanol and 75 ml toluene to give 60.0 g (86% yield) 3-(3-iodo-2-propynyloxy)-pyridine, mp 130° C. with decomposition.

Analysis calculated for: $C_8H_6INO$: I, 48.99. Found: I, 49.16.

EXAMPLE XII

Preparation of 3-(3-iodo-2-propynyloxy)-6-methylpyridine

A solution of 160 g (1.10 moles) 6-methyl-3-(2-propynyloxy) pyridine and 2000 ml methanol was cooled to 0° C. and 750 g 25% sodium hydroxide solution was slowly added. Iodine (362 g. 1.4 moles) was added portionwise and the resulting suspension stirred at 0°-10° C. for an additional 30 min. The reaction mixture was then poured into 4000 ml water and the solids filtered to give 250 g 3-(3-iodo-2-propynyloxy)-6-methylpyridine. Yield=90% Recrystallization from methanol gave analytically pure material, mp 155°-157° C.

Analysis calculated for: $C_9H_8INO$: C, 39.58; H, 2.95 I, 46.47; N, 5.13. Found: C, 39.80; H, 2.92 I, 46.47; N, 5.12.

EXAMPLE XIII

Preparation of 2-chloro-3-(3-iodo-2-propynyloxy)pyridine

In a manner similar to Example 12, 2-chloro-3-(2-propynyloxy)pyridine was converted to 2-chloro-3-(3-iodo-2-propynyloxy)pyridine, mp 164°-165° C.

Analysis calculated for $C_8H_5ClINO$: C, 32.70; H, 1.71; N, 4.78. Found: C, 33.00; H, 1.77; N, 4.76.

EXAMPLE XIV

Preparation of 2-chloro-3-(3-iodo-2-propynyloxy)-6-methylpyridine

In a manner similar to Example XII, 2-chloro-3-(2-propynyloxy)-6-methylpyridine was converted to 2-chloro-3-(3-iodo-2-propynyloxy)-6-methylpyridine, mp 130°-132° C.

Analysis calculated for: $C_9H_7ClINO$: C, 35.15; H, 2.29; Cl, 11.53; I, 41.27; N, 4.56. Found: C, 35.41; H, 2.34; Cl, 11.47; I, 41.25; N, 4.53.

EXAMPLE XV

Preparation of 2-amino-3-(3-iodo-2-propynyloxy)pyridine

In a manner similar to Example XII, 2-amino-3-2-propynyloxy)pyridine was converted to 2-amino-3-(3-iodo-2-propynyloxy)pyridine, mp 140° C.

Analysis calculated for: $C_8H_7IN_2O$: C, 35.06; H, 2.57; I, 45.30; N, 10.22 Found: C, 35.57; H, 2.65; I, 45.34; N, 10.11.

EXAMPLE XVI

Preparation of 3-(3-iodo-2-propynylthio)pyridine

In a manner similar to Example XII, 3-(2-propynylthio)pyridine was converted to 3-(3-iodo-2-propynylthio)pyridine, mp 114°-116° C.

Analysis calculated for: $C_8H_{16}INS$: C, 34.92; H, 2.20; N, 5.09; S, 11.62. Found: C, 34.25; H, 2.52; N, 5.26; S, 12.23.

EXAMPLE XVII

Preparation of 3-(3-iodo-2-propynyloxymethyl)pyridine

In a manner similar to Example XII, 3-(2-propynylmethyl)pyridine was converted to 3-(3-iodo-2-propynyloxymethyl)pyridine, mp 109°-110° C.

Analysis calculated for: $C_9H_8INO$: C, 39.58; H, 2.95; I, 46.48; N, 5.13. Found: C, 40.01; H, 3.00; I, 46.49; N, 5.24.

EXAMPLE XVIII

Preparation of 4-(3-iodo-2-propynyloxy)pyridine

In a manner similar to Example XII, 4-(2-propynyloxy)pyridine was converted to 4-(3-iodo-2-propynyloxy)pyridine, mp 140°-141° C.

Analysis calculated for: $C_8H_6INO$: C, 37.09; H, 2.33; N, 5.41. Found: C, 36.88; H, 2.24; N, 5.28.

EXAMPLE XIX

Preparation of 4-(3-iodo-2-propynylthio)pyridine

In a manner similar to Example XII, 4-(2-propynylthio)pyridine was converted to 4-(3-iodo-2-propynylthio)pyridine, mp 140° C.

Analysis calculated for $C_8H_6INS$: S, 11.66. Found: S, 11.18.

B. The following examples illustrate the utility of the novel iodopropargyl compounds of this invention.

EXAMPLE XX

General Antimicrobial Activity

Antibacterial and antifungal activity were evaluated by a 5-fold serial dilution test in agar. In this test, compounds were prepared as 6% solutions in dimethylformamide or ethanol. The 6% solution was then 5-fold serially diluted in test tubes to give the desired concentrations when mixed with agar and poured into sterile Petri dishes. Trypticase glucose extract agar was used for the bacterial testing; mildew glucose agar for the fungal testing. The bacterial plates were spot inoculated with 24-hour nutrient broth cultures and incubated at 37° C. for 48 hours. The fungal plates were spot inoculated with spore suspensions and incubated at 28° C. for seven days. At the end of the incubation periods, all plates were examined for growth. The minimum inhibitory concentration (MIC) for each organism is expressed in Table I. In the ranges presented, growth is observed only at the lower concentration.

TABLE I

| R—Q—CH$_2$C≡CI Compound | Minimum Inhibitory Concentration Range | | | | | | | | |
|---|---|---|---|---|---|---|---|---|---|
| | Bacteria | | | | | Fungi | | | |
| R—Q— | B$_1$ | B$_2$ | B$_3$ | B$_4$ | B$_5$ | F$_1$ | F$_2$ | F$_3$ | F$_4$ |
| 1 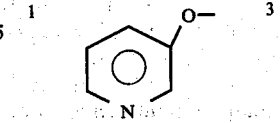 O— | 3 | 2 | 0 | 4 | 4 | 7 | 6 | 6 | 6 |

TABLE I-continued

| # | R-Q- | B1 | B2 | B3 | B4 | B5 | F1 | F2 | F3 | F4 |
|---|------|----|----|----|----|----|----|----|----|----|
| 2 | 6-methylpyridin-3-yl-O- | 0 | 0 | 0 | 0 | 0 | 8 | 8 | 7 | 8 |
| 3 | 3-chloropyridin-2-yl-O- | 4 | 3 | 0 | 4 | 4 | 8 | 7 | 6 | 6 |
| 4 | 3-chloro-6-methylpyridin-2-yl-O- | 1 | 0 | 0 | 0 | 3 | 8 | 7 | 6 | 7 |
| 5 | 3-aminopyridin-2-yl-O- | 3 | 3 | 2 | 4 | 3 | 6 | 6 | 5 | 5 |
| 6 | pyridin-3-yl-S- | 0 | 0 | 0 | 0 | 0 | 3 | 8 | 6 | 6 |
| 7 | pyridin-3-yl-CH₂—O- | 2 | 2 | 0 | 3 | 2 | 7 | 6 | 6 | 5 |
| 8 | pyridin-2-yl-O- | 1 | 1 | 0 | 2 | 4 | 8 | 7 | 7 | 6 |
| 9 | pyridin-3-yl-S- | 1 | 0 | 0 | 1 | 2 | 8 | 6 | 6 | 6 |

Key to Table I
The Microorganisms Tested

| Bacteria | | Fungi | |
|---|---|---|---|
| B1 | Staphylococcus aureus | F1 | Aspergillus niger |
| B2 | Escherichia coli | F2 | Aspergillus oryzae |
| B3 | Pseudomonas aeruginosa | F3 | Penicillium piscarium |
| B4 | Proteus vulgaris | F4 | Aureobasidium pullulans |
| B5 | Bacillus subtilis | | |

The Activity Levels Defined

| Activity Level | Growth At | No Growth At |
|---|---|---|
| 0 | >1920 µg/ml | |
| 1 | 384 µg/ml | 1920 µg/ml |
| 2 | 76 µg/ml | 384 µg/ml |
| 3 | 15 µg/ml | 76 µg/ml |
| 4 | 3 µg/ml | 15 µg/ml |
| 5 | 0.6 µg/ml | 3 µg/ml |
| 6 | 0.12 µg/ml | 0.6 µg/ml |
| 7 | 0.03 µg/ml | 0.12 µg/ml |
| 8 | | <.03 µg/ml |

EXAMPLE XXI

Antifungal Activity on Painted Surfaces

Any antifungal agent which can be used to prevent mildew on painted surfaces must be effective against *Aureobasidium pullulans*, the organism which is primarily responsible for mildew on painted surfaces.

The effectiveness of the novel compounds was treated by incorporating the compound into an exterior latex paint, applying the paint to a surface, and testing the ability of the painted surface to prevent the growth of *Aureobasidium pullulans*. The tests were run as described below.

The novel compounds were incorporated into an exterior vinyl acetate latex paint by mulling the compound into the paint. The compounds were tested in the paints at levels of 0.25% and 0.5%.

One coat of this paint was applied to each side of a piece of Whatman #30 filter paper. Two one-inch squares were cut from the filter paper. Each square was centered on the agar surface of separate Petri dishes containing malt agar. One square was inoculated with a suspension of *Aureobasidium pullulans* (strain 1) which was an in-house strain used for routine antimicrobial testing. The second square was inoculated with a suspension of *Aureobasidium pullulans* (strain 2) which was grown from a culture obtained from the surface of a mildew infested panel. Squares painted with the same exterior vinyl acetate latex paint, but without the novel compounds of this invention, were run in parallel. The Petri dishes were then incubated at 27° C. and at greater than 90% humidity for a three week period and observed for zones of inhibition and surface growth.

Table II clearly shows that the compounds of this invention prevented mildew growth on the painted surfaces. In contrast, those surfaces painted with the paint which did not contain the compounds of this invention did not prevent mildew growth.

TABLE II

| Compound (R—Q—CH₂C≡Cl) R—Q— | Zone of Inhibition/ Surface Growth @ | | | |
|---|---|---|---|---|
| | 0.5% | | 0.25% | |
| | Strain 1 | Strain 2 | Strain 1 | Strain 2 |
| pyridin-2-yl-O- | 3/0 | — | 3/0 | — |
| 6-methylpyridin-3-yl-O- | 2/0 | 2/0 | 2/0 | 1/0 |
| 3-chloropyridin-2-yl-O- | 3/0 | 2/0 | 2/0 | 1/0 |
| 3-aminopyridin-2-yl-O- | 2/0 | 0/0 | 0/0 | 0/0 |
| pyridin-3-yl-S- | 3/0 | 2/0 | 2/0 | 0/0 |
| pyridin-3-yl-CH₂O- | 5/0 | 4/0 | 4/0 | 3/0 |
| pyridin-2-yl-O- | 2/0 | 1/0 | — | — |

TABLE II-continued

| | | | | |
|---|---|---|---|---|
| ![pyridyl-S-] | 1/0 | 0/0 | 0/0 | 0/0 |
| Control[b] | 0/3 | 0/3 | 0/3 | 0/3 |

[a] Key for Table II

| Zone of Inhibition | Surface Growth |
|---|---|
| 0 : no zone | 0 : No growth |
| 1 : 1-5 mm | |
| 2 : 6-10 mm | 1 : Slight growth |
| 3 : 11-15 mm | 2 : Moderate growth |
| 4 : 16-20 mm | 3 : Heavy growth |
| 5 : >20 mm | |

[b] The control is vinyl acetate latex paint without a compound of this invention.

[c] The "—" indicates that there was no data obtained.

EXAMPLE XXII

Successful paint fungicides must be stable when exposed to the elements such as heat and light. Such stability was tested in the laboratory by exposing painted sticks to heat and light.

The compounds of this invention were incorporated into an exterior vinyl acetate latex paint as described in Example XXI. Birch blades (tongue depressors) were painted (two coats) and continuously exposed to light (wavelength 300-400 nm) and heat (40° C.) for four consecutive weeks.

At the end of the exposure time, one-inch squares of the painted birch blades were cut and tested according to the procedure of Example XXI, using strain 2. The results are summarized in Table III.

TABLE III

| Compound R—Q—CH$_2$C≡CI | Zone of Inhibition/ Surface Growth[a] | |
|---|---|---|
| R—Q— | 0.5% | 0.25% |
| pyridyl-3-O— | 1/0 | 0/0 |
| 2-methyl-pyridyl-O— | — | 0/0 |
| 3-chloro-pyridyl-O— | — | 0/0 |
| 3-chloro-2-methyl-pyridyl-O— | 0/0 | — |
| 2-amino-pyridyl-O— | 0/0 | 0/1 |
| pyridyl-S— | 0/2 | 0/3 |
| pyridyl-CH$_2$O— | 1/0 | 0/0 |

TABLE III-continued

| Compound R—Q—CH$_2$C≡CI | Zone of Inhibition/ Surface Growth[a] | |
|---|---|---|
| R—Q— | 0.5% | 0.25% |
| pyridyl-2-O— | 0/2 | 0/2 |
| phenyl-O—[b] | 0/2 | 0/3 |
| Control | 0/3 | — |

[a] Key is the same as for Table II.

[b] This is 3-iodo-2-propynyloxybenzene.

EXAMPLE XXIII

A number of the compounds were field tested in various latex paints. Pine panels (6"×12"×½") were given two coats of paint and, after drying, were exposed at an outdoor location subject to high heat and humidity levels. Paints containing the novel compounds of this invention were compared with those containing the commercial mecurial mildewcide phenyl mecuric acetate (PMA), a commercial non-mercurial mildewcide 2-n-octyl-4-isothiazolin-3-one and 3-iodo-2-propynyloxybenzene.

Table IV shows the results over a six-month period. Clearly, the compounds of this invention proved to be superior under these test conditions.

The symbols used in Table IV are as follows:

| Paints | Panel Scoring |
|---|---|
| A — Vinyl acetate latex | 10 — No mildew on surface |
| B — Acrylic latex-alkyd modified | 9 — Very slight growth |
| C — Vinyl latex-alkyd modified | 8 — Slight growth |
| | 6 — Definite growth |
| | 4 — Medium growth |
| | 2 — Bad growth |
| | 0 — Very bad growth |

TABLE IV

Outdoor Testing

| | | | Month | | | | | |
|---|---|---|---|---|---|---|---|---|
| Comp[a] | Paint | Conc. | 1 | 2 | 3 | 4 | 5 | 6 |
| 1 | A | .5% | 10 | 10 | 10 | 10 | 10 | 10 |
| 2 | A | .5% | 10 | 10 | 10 | 10 | 10 | 10 |
| 3 | A | .5% | 10 | 10 | 10 | 10 | 10 | 10 |
| 4 | A | .4% | 10 | 10 | 10 | 10 | 10 | 10 |
| I | A | .5% | 10 | 10 | 10 | 9 | 4 | 4 |
| II | A | .5% | 10 | 10 | 9 | 8 | 4 | 2 |
| III | A | .5% | 10 | 6 | 4 | 2 | 2 | 2 |
| Control | A | — | 2 | 0 | 0 | 0 | 0 | 0 |
| 1 | B | .5% | 10 | 10 | 10 | 9 | 8 | 8 |
| 2 | B | .5% | 10 | 10 | 10 | 10 | 10 | 10 |
| II | B | .5% | 10 | 10 | 10 | 9 | 6 | 4 |
| III | B | .5% | 10 | 9 | 4 | 4 | 2 | 0 |
| Control | B | — | 2 | 0 | 0 | 0 | 0 | 0 |
| 1 | C | .5% | 10 | 10 | 10 | 10 | 10 | 10 |
| 2 | C | .5% | 10 | 10 | 10 | 10 | 10 | 10 |
| II | C | .5% | 10 | 10 | 10 | 10 | 4 | 2 |
| III | C | .5% | 10 | 10 | 6 | 2 | 2 | 2 |

TABLE IV-continued

| | | | Outdoor Testing | | | | | |
|---|---|---|---|---|---|---|---|---|
| | | | | Month | | | | |
| Comp.@ | Paint | Conc. | 1 | 2 | 3 | 4 | 5 | 6 |
| Control | C | — | 4 | 2 | 0 | 0 | 0 | 0 |

@ Novel Compounds
1 3-(3-iodo-2-propynyloxy)pyridine
2 3-(3-iodo-2-propynyloxy)-6-methylpyridine
3 2-chloro-3-iodo-2-propynyloxy)pyridine
4 2-chloro-3-(3-iodo-2-propynyloxy)-6-methylpyridine
Comparison Compounds
I phenyl mercuric acetate
II 2-n-octyl-4-isothiazolin-3-one
III 3-iodo-2-propynyloxybenzene

We claim:

1. A compound of the formula:

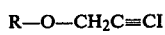

wherein R is a 3-pyridyl radical.

2. A compound of claim 1 wherein the substituents on the aromatic ring of the 3-pyridyl group are selected from the group consisting of hydrogen, halogen, lower alkyl from one to four carbons and amino.

3. A compound of claim 2 wherein the substituents on R are selected from the group consisting of hydrogen, methyl, chloro and amino.

4. A compound of claim 3 having the structure:

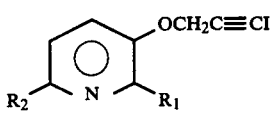

wherein:
R₁ is chosen from the group consisting of H, Cl, and NH₂; and
R₂ is H or CH₃.

5. A compound of claim 4 having the structure

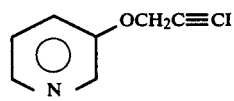

6. A compound of claim 4 having the structure

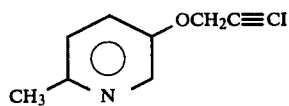

7. A compound of claim 4 having the structure

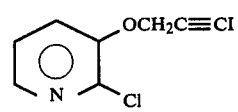

8. A compound of claim 4 having the structure

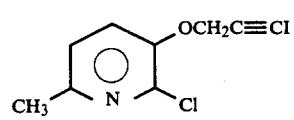

9. A compound of claim 4 having the structure

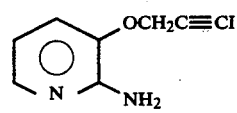

10. A compound of the formula:

R—O—CH₂—C≡CI wherein R is a picolyl group.

11. A compound of claim 10 having the structure

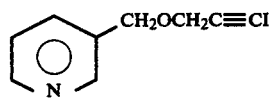

12. A compound of of the formula

wherein R is a pyridyl or picolyl group.

13. A compound of claim 12 having the structure

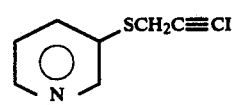

14. A compound of claim 12 having the structure

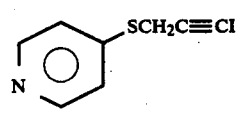

15. A compound of the formula:

wherein R is a 3-pyridyl radical.

16. A compound of claim 15 having the formula:

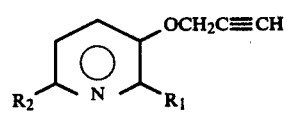

wherein:
R₁ is chosen from the group consisting of H, Cl, and NH₂; and
R₂ is H or CH₃.

17. A compound of claim 16 having the structure

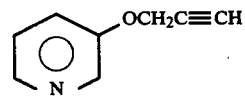

18. A compound of claim 16 having the structure

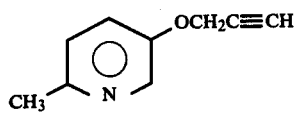

19. A compound of claim 16 having the structure

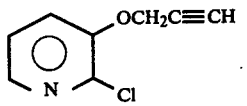

20. A compound of claim 16 having the structure

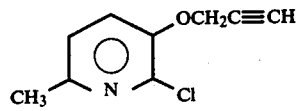

21. A compound of claim 16 having the structure

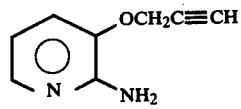

22. A compound of the formula

R—O—CH₂C≡CH wherein R is a picolyl group.

23. A compound of claim 22 having the structure

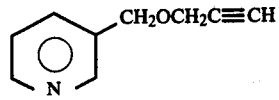

24. A compound of the formula:

R—S—CH₂C≡CH wherein R is a pyridyl or picolyl group.

25. A compound of claim 24 having the structure

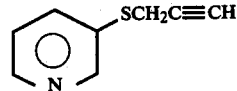

26. A compound of claim 24 having the structure

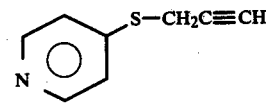

* * * * *